United States Patent
John et al.

(10) Patent No.: US 9,474,271 B2
(45) Date of Patent: Oct. 25, 2016

(54) METHOD FOR ENHANCING AMIDOHYDROLASE ACTIVITY OF FATTY ACID AMIDE HYDROLASE

(71) Applicant: Research Foundation of the City University of New York, New York, NY (US)

(72) Inventors: George John, New York, NY (US); Subbiah Nagarajan, New York, NY (US); Kent Chapman, Denton, TX (US); Lionel Faure, Flower Mound, TX (US); Peter Koulen, Leawood, KS (US)

(73) Assignees: Research Foundation of the City University of New York, New York, NY (US); The Curators of The University of Missouri, Columbia, MO (US); University of North Texas, Denton, TX (US)

( * ) Notice: Subject to any disclaimer, the term of this patent is extended or adjusted under 35 U.S.C. 154(b) by 0 days.

(21) Appl. No.: 14/761,826

(22) PCT Filed: Jan. 17, 2014

(86) PCT No.: PCT/US2014/012074
§ 371 (c)(1),
(2) Date: Jul. 17, 2015

(87) PCT Pub. No.: WO2014/113689
PCT Pub. Date: Jul. 24, 2014

(65) Prior Publication Data
US 2015/0359218 A1    Dec. 17, 2015

Related U.S. Application Data

(60) Provisional application No. 61/754,252, filed on Jan. 18, 2013, provisional application No. 61/898,935, filed on Nov. 1, 2013.

(51) Int. Cl.
*A01N 47/10* (2006.01)
*A01N 37/20* (2006.01)
*A01N 39/04* (2006.01)
*A61K 31/165* (2006.01)

(52) U.S. Cl.
CPC ............... *A01N 37/20* (2013.01); *A01N 39/04* (2013.01); *A61K 31/165* (2013.01)

(58) Field of Classification Search
None
See application file for complete search history.

(56) References Cited

U.S. PATENT DOCUMENTS

| | | |
|---|---|---|
| 2005/0028233 A1 | 2/2005 | Chapman et al. |
| 2005/0131032 A1 | 6/2005 | Sit et al. |
| 2005/0154064 A1 | 7/2005 | Piomelli et al. |
| 2007/0134753 A1 | 6/2007 | Barbier et al. |

OTHER PUBLICATIONS

Cimpan et al.(Role of stationary phase and eluent composition on the determination of log P values of N-hydroxyethylamide of aryloxyalkylen and pyridine carboxylic acids by reversed-phase HPLC), J. of Chromatography B, 714, 1998, pp. 247-261.*
Marzo et al; Endocannabinoids and Related Compounds: Walking Back and Forth between Plant Natural Products and Animal Physiology; Chemistry & Biology; vol. 14; pp. 741-756, Jul. 2007.
US/ISA; International Search Report for PCT/US2014/012074; May 6, 2014.

* cited by examiner

*Primary Examiner* — Alton Pryor
(74) *Attorney, Agent, or Firm* — Peter J. Mikesell; Schmeiser, Olsen & Watts, LLP

(57) ABSTRACT

A method for enhancing amidohydrolase activity of Fatty Acid Amide Hydrolase (FAAH) is disclosed. The method comprising administering a phenoxyacylethanolamide that causes the enhanced activity. The enhanced activity can have numerous effects on biological organisms including, for example, enhancing the growth of certain seedlings. The subject matter disclosed herein relates to enhancers of amidohydrolase activity.

11 Claims, 11 Drawing Sheets

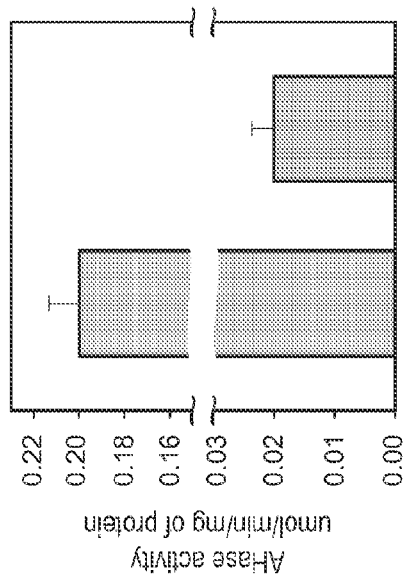
FIG. 2A
FIG. 2B
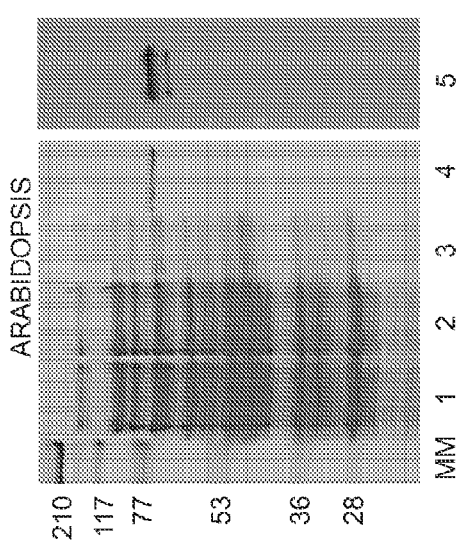
FIG. 2C

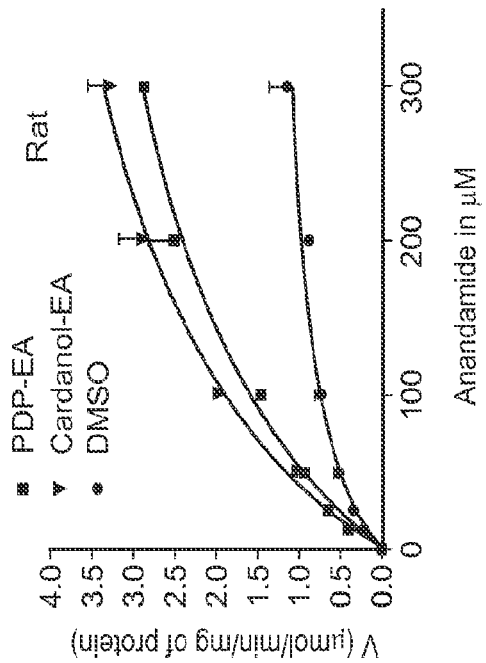
FIG. 6A
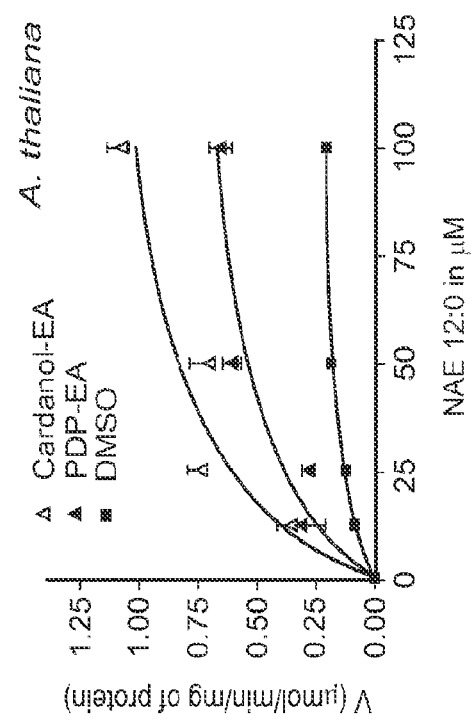
FIG. 6B
| | $K_m^{app} \mu M$ | $V_{max}^{app}$ | $K_{cat} s^{-1}$ | $K_{cat}/K_m M^{-1} s^{-1}$ | $K_m^{app} \mu M$ | $V_{max}^{app}$ | $K_{cat} s^{-1}$ | $K_{cat}/K_m M^{-1} s^{-1}$ |
|---|---|---|---|---|---|---|---|---|
| DMSO | 26 ± 5.09 | 0.26 ± 0.014 | 1 | 3.8x10$^4$ | 56 ± 7.07 | 1.38 ± 0.14 | 4.8 | 8.57x10$^4$ |
| PDP-EA | 37 ± 9.8 | 0.89 ± 0.16 | 3.4 | 9.18x10$^4$ | 173 ± 18 | 4.9 ± 0.56 | 17 | 9.8x10$^4$ |
| Cardanol-EA | 34 ± 2.8 | 1.4 ± 0.18 | 5.4 | 1.58x10$^5$ | 179 ± 25 | 5.4 ± 0.49 | 18.75 | 1.04x10$^5$ |
FIG. 6C

METHOD FOR ENHANCING AMIDOHYDROLASE ACTIVITY OF FATTY ACID AMIDE HYDROLASE

CROSS-REFERENCE TO RELATED APPLICATIONS

This application claims priority to U.S. Patent Application Ser. No. 61/754,252 (filed Jan. 18, 2013) and U.S. Patent Application Ser. No. 61/898,935 (filed Nov. 1, 2013). The entirety of each of the aforementioned patent applications is hereby incorporated herein by reference.

STATEMENT OF FEDERALLY SPONSORED RESEARCH OR DEVELOPMENT

This invention was made with U.S. Federal Government support under contract number EY022774 awarded by the NIH National Eye Institute; contract numbers AG022550 and AG027956 awarded by the NIH Institute on Aging; contract number DE-FG02-05ER15647 awarded by the Department of Energy and Contract No. 1046099 awarded by NSF-CBET. The government has certain rights in the invention.

BACKGROUND OF THE INVENTION

The subject matter disclosed herein relates to enhancers of amidohydrolase activity. Fatty acid amide hydrolase (FAAH) belongs to the superfamily of amidase signature proteins. FAAH enzymes are found in diverse groups of organisms including both plants and animals. FAAH enzymes hydrolyze a broad range of N-acylethanolamines (NAEs) to corresponding free fatty acid and ethanolamine, and can also act on primary acyl amides as well as acyl esters. In plants, one type of FAAH has been characterized, whereas two distinct FAAHs have been described in animal systems. The homology between plant (Arabidopsis) and mammalian (rat) FAAH proteins at the amino acid level is somewhat low over the full length of the proteins. However, the amidase signature sequence (with core catalytic residues) between plant and animal FAAH share up to 60% similarity at the amino acid level. The X-ray crystallography data of the rat protein provided new insights about the mode of action of this enzyme in NAE hydrolysis. Although no tertiary structure has been determined yet for plant FAAH, a structural homology model was developed for the amidase domain of the Arabidopsis FAAH protein and conserved catalytic residues were identified experimentally.

The activity of FAAH is a key regulatory feature of the NAE signaling pathway. The regulated accumulation of NAEs influences numerous functions in plants and animals. The functional activities and physiological effects of NAEs are mostly terminated by their degradation to FFA and ethanolamine. In plants, NAEs are involved in seedling establishment and growth. Exogenously applied N-lauroylethanolamine (NAE 12:0) arrests seedling growth and this is evident through marked changes in root architecture and elongation. This inhibitory effect of NAEs on seedling growth occurs in part through a complex interaction with ABA (abscisic acid) signaling machinery during the embryo-to-seedling transition that remains incompletely understood. On the other hand, reductions of endogenous seed NAE levels through the over-expression of FAAH in Arabidopsis results in enhanced seedling growth and increased size of roots, cotyledons and other plant organs. Other physiological processes have been attributed to FAAH mediated alteration of NAE levels in plants, such as flowering time which is induced by the expression and translocation of the FLOWERING LOCUS T (FT) protein from leaves to the vegetative meristem. FAAH over-expressing plants exhibited an early flowering phenotype in both inductive and non-inductive growth conditions, and this was associated with lower NAE levels and higher expression of FT and other key flowering genes. Still other work has attributed changes in host susceptibility to pathogens or changes in phytohormone signaling pathways with altered FAAH expression.

In animals, FAAH-mediated NAE changes are part of the so-called "endocannabinoid signaling pathway", and this pathway plays a central regulatory role in many physiological and behavioral processes. The most widely studied NAE in animal systems is the N-arachidonylethanolamine, known also as anandamide (NAE 20:4), but other NAE species with overlapping or unique functions are known as well. As an example N-linoleoylethanolamine (NAE 18:2) or N-palmitoylethanolamine (NAE 16:0) are involved in neuron protection in the retinal ganglion cell layer against excessive extracellular glutamate and against oxidative stress for the HT22 cells, respectively. Anandamide was identified as the first endogenous ligand of the cannabinoid receptors (CB1 and CB2), and is involved in activating many of the important endocannabinoid pathways. Anandamide and other NAEs have been associated with different processes such as pain modulation, memory, anxiety, appetite, etc. Their levels are controlled largely through hydrolysis by FAAH. Thus, FAAH has become a major therapeutic target for many disorders that involves NAE signaling in situ.

Several approaches have been employed to increase the level of NAEs in plants or animals including the direct application of NAEs or pharmacological reagents that inhibit NAE degradation. Utilization of general and/or specific inhibitors of FAAH activity such as phenylmethylsulfonyl fluoride (PMSF), 5Z,8Z,11Z,14Z-eicosatetraenylmethyl ester phosphonofluoridic acid (MAFP) or 3'-(aminocarbonyl)[1,1'-biphenyl]-3-yl)-cyclohexylcarbamate (URB597) have been reported to elevate endogenous levels of NAE, and to extend or amplify processes regulated by NAE signaling. Genetic approaches have been developed to reduce FAAH expression (FAAH knockouts) in mice and Arabidopsis, although this approach has shown limited success, especially in plants where it appears that there are redundant pathways for NAE catabolism, and where it has been difficult to raise endogenous NAE levels dramatically in vivo. On the other hand, it has been possible to over-express FAAH in plants and reduce NAE levels to some extent to influence several physiological processes including growth, defense, and flowering. However, there is limited information on chemical compounds that reduce the NAE content in plant and animal systems via enhanced FAAH activity.

Among the multitude of renewable resources, cashew nutshell liquid (CNSL) is an important by-product of the cashew nut industry that is currently used for green chemicals and technologies. More than 32% of the cashew shell is CNSL, the key constituent of CNSL being cardanol, a bio based non isoprene lipid, comprising a rich mixture of phenolic lipids: 5% of 3-(pentadecyl)-phenol (3-PDP), 50% of 3-(8Z-pentadecenyl)phenol, 16% of 3-(8Z,11Z-pentadecadienyl)phenol and 29% of 3-(8Z,11Z,14-pentadecatrienyl)phenol. Cardanol's unique properties stem from the varying degree of cis-double bonds and an odd number of hydrocarbons with easily accessible saturated and unsaturated hydrocarbon chains.

The discussion above is merely provided for general background information and is not intended to be used as an aid in determining the scope of the claimed subject matter.

BRIEF DESCRIPTION OF THE INVENTION

A method for enhancing amidohydrolase activity of Fatty Acid Amide Hydrolase (FAAH) is disclosed. The method comprising administering a phenoxyacyl-ethanolamide that causes the enhanced activity. The enhanced activity can have numerous effects on biological organisms including, for example, enhancing the growth of certain seedlings.

Disclosed in this specification is a method for enhancing amidohydrolase activity of fatty acid amide hydrolase. The method comprises steps of administering a phenoxyacyl-ethanolamide composition to a biological organism such that hydrolysis of N-acylethanolamines (NAEs) by fatty acid amide hydrolase (FAAH) in the biological organism is enhanced relative to a substantially identical biological organism that has not been administered with the phenoxyacyl-ethanolamide composition.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 2A, FIG. 2B and FIG. 2C are SDS-PAGE and Western blots of the enriched At-FAAH1 or rat FAAH from E. coli on a 12.5% polyacrylamide gel; wherein FIG. 2A, is a SDS-PAGE and western blot of different fractions of the plant FAAH protein purification; FIG. 2B is a SDS-PAGE and western blot of different fractions of the rat FAAH protein purification, wherein Lane 1, supernatant (lysis); lane 2, flow through; Lane 3, wash fraction; Lane 4 eluted fraction; MM, molecular marker (molecular weight are represented in kilodaltons); lane 5, western blot probed with mouse monoclonal anti-HIS antibodies;

FIG. 2C shows a "Detergent effect" (Triton X-100) on the amidohydrolase activity (AHase) of the At-FAAH in presence of PDP-EA or cardanol-EA, wherein reactions were initiated by addition of 0.3 µg of purified protein extracted with 1% Triton X-100 or with 0.2 mM of DDM in the presence of 100 µM of PDP-EA (or cardanol-EA); reactions were carried out in 50 mM BisTris propane-HCl (pH 9.0), 0.2 mM DDM at 30° C. for 30 minutes in a final volume of 0.15 ml; data points represent means±S.D. of triplicate assays; plots were generated with SigmaPlot software version 12.0;

FIGS. 4A to 4G illustrate representative radiochromatograms of the total $[1\text{-}^{14}C]$-lipid components of following FAAH reactions in presence (or absence) of 100 µM of PDP-EA or cardanol-EA; reactions were initiated by the addition of purified rat or At-FAAH protein (0.3 µg) with 50 mM of Bis-Tris propane-HCl (pH 9.0), 0.2 mM DDM and 100 µM $[1\text{-}^{14}C]$-NAE 12:0 in a final volume of 0.15 ml; reactions proceeded at 30° C. with shaking (120 rpm) for 25 min; wherein FIGS. 4A to 4C show a reaction with At-FAAH protein, solvent control (DMSO); with 100 µM of PDP-EA; with 100 µM of cardanol-EA; FIG. 4D to 4F show a reaction with rat FAAH protein, solvent control (DMSO); with 100 µM of PDP-EA; with 100 µM of cardanol-EA; FIG. 4G shows assays with heat-denatured At-FAAH protein (5 minutes at 100° C.) plus cardanol-EA (100 µM); lipids were extracted and separated by TLC (60:40:5; v/v/v); chromatograms were obtained by radiometric scanning of the TLC plate;

FIGS. 5A and 5B depict amidohydrolase activity (µmol/min/mg of protein) of purified At-FAAH or rat FAAH protein with different $[1\text{-}^{14}C]$-N-acylethanolamines (NAEs) in presence of 100 µM of PDP-EA or cardanol-EA; wherein FIG. 5A shows assays with purified At-FAAH (0.3 µg); FIG. 5B shows assays with purified rat FAAH (0.3 µg); reactions were carried out in 50 mM BisTris propane-HCl (pH 9.0), 0.2 mM DDM at 30° C., 30 minutes, with shaking (120 rpm) in a final volume of 0.15 ml; data points represent means±S.D. of triplicate assays; plots were generated with SigmaPlot software version 12.0. P-value of <0.05, <0.01, is indicated by * and **, respectively, as determined by student's t test. ns, not significant.

FIGS. 6A, 6B and 6C depict a kinetic characterization of At-FAAH1p and rat FAAH in presence of 100 μM PDP-EA or cardanol-EA; initial velocities were measured at increasing concentrations of [1-$^{14}$C]-NAE 12:0 for At-FAAH (FIG. 6A); or [1-$^{14}$C]-NAE 20:4 for rat FAAH (FIG. 6B). Reactions were initiated by the addition of purified protein (0.3 μg). (FIG. 6C), represent the apparent kinetic parameters of the enzymes estimated by transformations of these original data (i.e., double-reciprocal plots). Reactions were carried out in 50 mM BisTris propane-HCl (pH 9.0), 0.2 mM DDM at 30° C. in a final volume of 0.15 ml. Data points represent means±S.D. of triplicate assays. Velocity in μmol/min/mg of protein. Plots were generated with Prism software version 3.0 (GraphPad Software, San Diego), and data were fitted to a nonlinear regression (curve fit) using one site binding (hyperbola) equation with a $R^2$ between 0.89 to 0.98 for the At-FAAH curves and between 0.93 to 0.98 for the rat curves;

FIG. 9A, Cardanol-EA pre-treatment exacerbates tBHP-mediated cell death; FIG. 9B, the bioactive lipid NAE 16:0, a substrate of FAAH, reverses this effect; FIG. 9C, FIG. 9D, Cardanol-EA treatment significantly reduces neuronal viability in anti-oxidant free media and exacerbates tBHP-mediated cell death; pre-incubation with the specific, irreversible, FAAH inhibitors MAFP and URB597 block this effect of cardanol-EA; data points represent means±SEM of triplicate assays; plots were generated with GraphPad Prism version 5.0; A P-value of <0.05, <0.01, and <0.001 is indicated by *, , and *, respectively, as determined by one-way ANOVA with Dunnett's post-test.

DETAILED DESCRIPTION OF THE INVENTION

N-Acylethanolamines (NAEs) are involved in numerous biological activities in plant and animal systems. The metabolism of these lipids by fatty acid amide hydrolase (FAAH) is a key regulatory point in NAE signaling activity. Several active-site-directed inhibitors of FAAH have been identified, but few compounds have been described that enhance FAAH activity. Disclosed in this specification are phenoxyacyl-ethanolamides synthesized from natural products, 3-N-pentadecylethanolamine (PDP-EA) and cardanolethanolamide (cardanol-EA), with structural similarity to NAEs. Their effects on the hydrolytic activity of FAAH were characterized. Both compounds increased the apparent $V_{max}$ of recombinant FAAH proteins from both plant (*Arabidopsis*) and mammalian (*Rattus*) sources. These NAE-like compounds appeared to act by reducing the negative feedback regulation of FAAH activity by free ethanolamine. Both compounds added to seedlings relieved, in part, the negative growth effects of exogenous NAE12:0. Cardanol-EA reduced neuronal viability and exacerbated oxidative stress-mediated cell death in primary cultured neurons at nanomolar concentrations. This was reversed by FAAH inhibitors or exogenous NAE substrate. Collectively, our data suggest that these phenoxyacyl-ethanolamides act to enhance the activity of FAAH and may stimulate the turnover of NAEs in vivo. Hence, these compounds might be useful pharmacological tools for manipulating FAAH-mediated regulation of NAE signaling in plants or animals.

Here, we synthesized a new set of phenoxyacyl-ethanolamides from this renewable resource with structural similarity to NAEs and investigated their effects on the FAAH activity. These phenoxyacyl-ethanolamides were not substrates for FAAH; however, we measured a positive effect of these compounds on NAE hydrolysis by recombinant FAAH. The increase in enzyme turnover rate likely is through relief from product inhibition by ethanolamine, a property not previously appreciated for either plant or mammalian FAAH enzymes. It is possible that compounds like these phenoxyacyl-ethanolamides, might prove useful in manipulating NAE levels in vivo through their actions on FAAH.

Phenoxyacyl-Ethanolamide Synthesis—

Figure 1A:
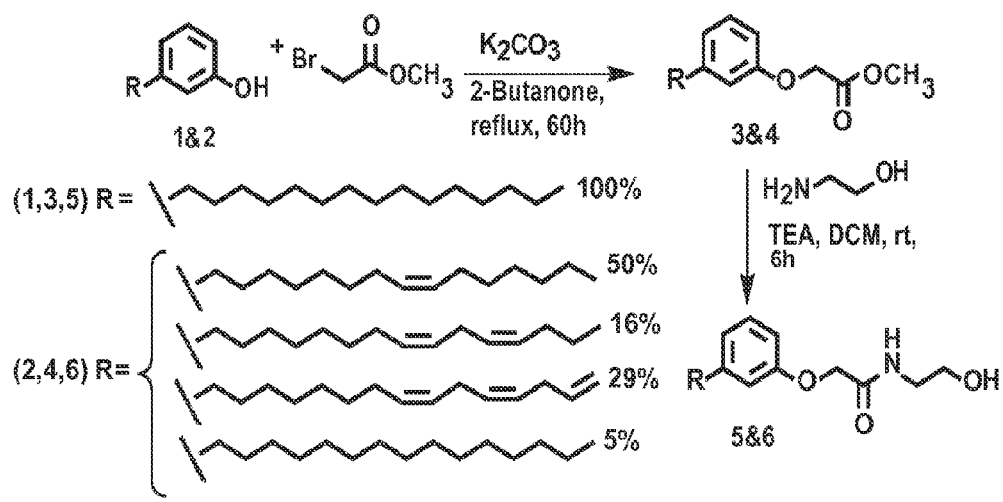
FIG. 1A depicts a chemical synthesis and structure of new NAE-like compounds; compound 1: 3-N-pentadecylphenol (PDP); compound 2: cardanol; compound 3: PDP-methylester; compound 4: cardanol-methylester; compound 5: 3-N-pentadecylphenolethanolamine (PDP-EA): [N-(2-hydroxyethyl)-2-(3-pentadecylphenoxyl)acetamide]; compound 6: cardanolethanolamine (cardanol-EA) (mixture of phenoxyacyl-ethanolamides); R, acyl chain.

We developed a simple method that proceeds by refluxing the mixture of phenolic lipids 3-PDP (compound 1 in FIG. 1A, where R is n-pentadecyl)) or cardanol (compound 2 in FIG. 1A, where R is $C_{15}H_{19}$ (50%); $C_{15}H_{25}$ (29%); $C_{15}H_{27}$ (16%); $C_{15}H_{31}$ (5%) and methylbromoacetate in the presence of $K_2CO_3$ as a base and 2-butanone as a solvent to generate the desired PDP-methylester 4 or cardanol-methylester 5. Amide bond formation of methylester by chemoselective reaction with ethanolamine as N-nucleophile in dry dichloromethane and triethylamine as base yielded the desired phenoxyacyl ethanolamides 5,6 in good yield and purity (supplemental data FIG. 1B and FIG. 1C). The products were separated by column chromatography and characterized by both NMR spectroscopy ($^1$H and $^{13}$C NMR) and mass spectrometric analysis. $^1$H NMR spectra of compound 5 and 6 (FIG. 1A) showed signals at δ 7.1 ppm for NH proton and δ 2.7 ppm for OH proton respectively. The exchangeable nature of these protons was identified using $D_2O$ exchange studies. High resolution mass spectral analysis of PDP-EA and cardanol-EA showed a molecular ion peak (M+H$^+$) at m/z 406.3321 and m/z 404.3163 respectively, which exactly matches with the theoretically calculated value (PDP-EA: [M+H]$^+$, m/z 406.3321 & cardanol-EA: [M+H]$^+$, m/z 404.3165). These new NAE-like compounds, named as 3-N-pentadecylphenolethanolamine (PDP-EA, 406.3 g·mol$^{-1}$) and cardanol-ethanolamide (cardanol-EA 404.3 g·mol$^{-1}$), were dissolved as 10 mM stock solutions in DMSO for assays.

Protein Purification and Amidohydrolase Assays—

Enzymatic assays were performed with two different purified recombinant proteins: *Arabidopsis thaliana* FAAH (AT-FAAH) (UniProt # Q7XJJ7) and rat FAAH (NCB accession # NP_077046). Expression and purification of these proteins were monitored by SDS PAGE and Western blotting (FIG. 2A and FIG. 2B). Bands observed in the SDS-PAGE gel are consistent with the molecular weights calculated for each protein plus the HIS tag (C-terminus of the protein), which are 70 kDa for At-FAAH and 66 kDa for rat FAAH. Both proteins were also detected by Western-blot using an anti-HIS tag monoclonal antibody with some unavoidable proteolytic degradation evident (FIG. 2A and FIG. 2B, lane 5). The inclusion of serine protease inhibitors was avoided so as not to influence FAAH activity.

Utilization of Triton X-100 during protein extraction is mandatory to recover the activity of the rat protein, but not for At-FAAH (supplemental data FIG. 2C). However, AHase assays performed with At-FAAH extracted in presence of 1% (v/v) Triton X-100 showed an increase by a factor of about 10 for hydrolysis of NAE to FFA compared to assays performed in 0.2 mM of DDM (supplemental data FIG. 2C). This increase of activity could be explained by improved solubilization of the protein, the lipophilic NAE substrate, and/or FFA product. For consistency and optimal activity, extraction of recombinant proteins in Triton X-100 was performed for all subsequent experiments.

Enhanced NAE Amidohydrolase Activity with the Plant or Rat FAAH in Presence of PDP-EA and Cardanol-EA—

Figure 3:
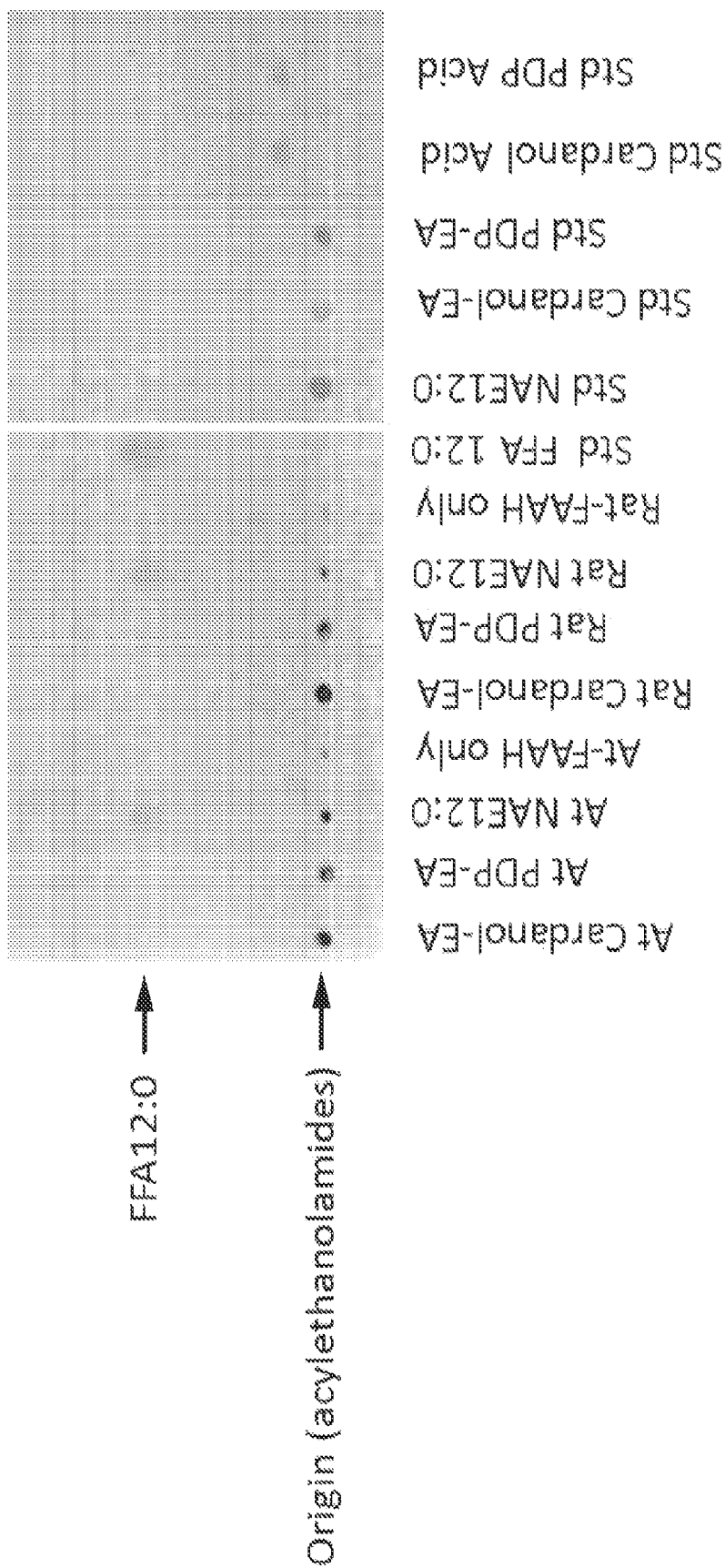
FIG. 3 illustrates a TLC analysis of the lipid composition of the amidohydrolase assay with At-FAAH or rat FAAH and different substrate; reactions were initiated by the addition of purified At-FAAH or rat FAAH protein (2 µg) with 50 mM of BisTris propane-HCl (pH 9.0), 0.2 mM DDM at 30° C. for 2 hours, 120 rpm and 200 µM different potential substrates in a final volume of 0.3 ml; lipids were extracted and then separated by TLC (hexane/diethyl ether/acid acetic, 80:20:2, v/v/v); positions of the origin (intact acylethanolamides) and the free fatty acid (FFA) 12:0 are indicated (arrows)

Neither of the NAE-like compounds (PDP-EA and cardanol-EA) appeared to be hydrolyzed to their respective acid forms (PDP-acid and cardanol-acid) and ethanolamine by either the plant or animal FAAH enzymes (2 μg protein and 100 μM-300 μM substrate) (FIG. 3). Somewhat surprisingly, compared to NAE 12:0, the phenoxyacyl-ethanolamides were not suitable substrates for FAAH as might be anticipated from the promiscuous nature of the FAAH enzymes.

Figure 4A:
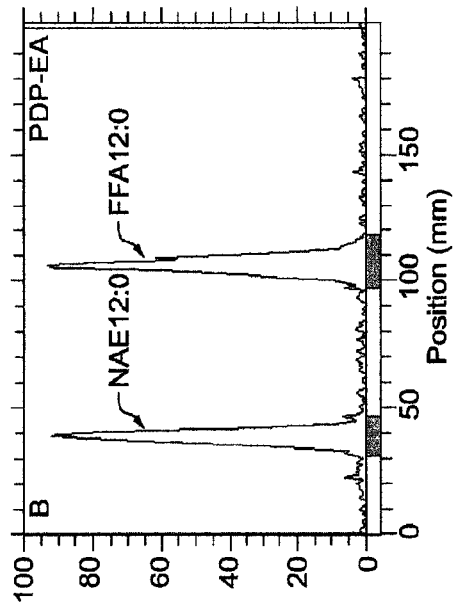
Figure 4B:
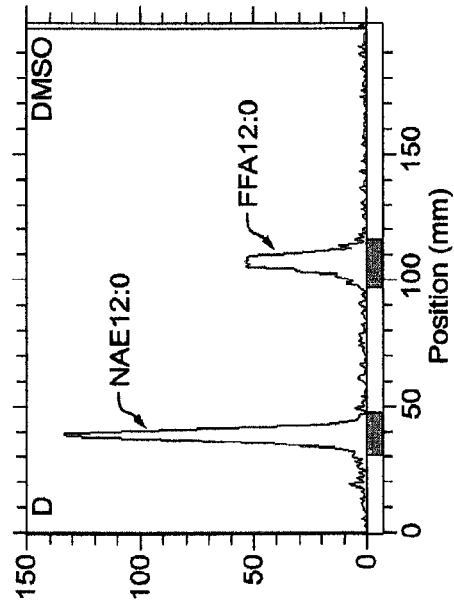
Figure 4C:
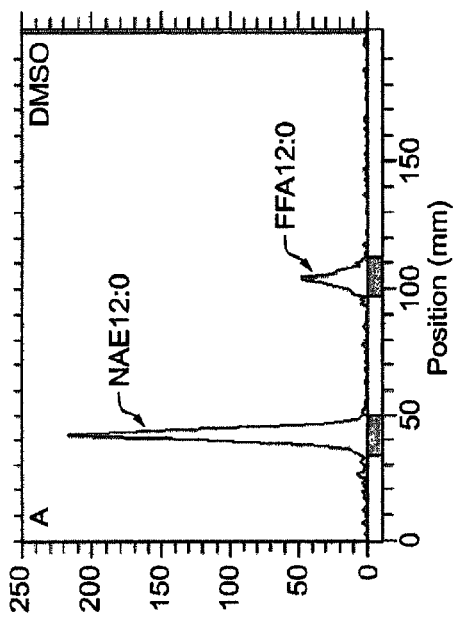
Figure 4D:
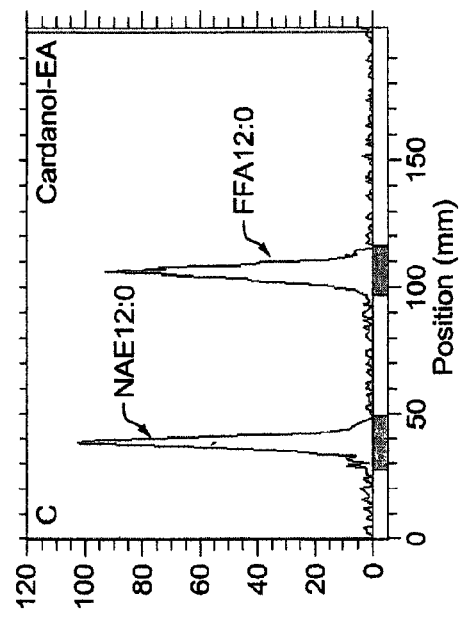
Figure 4F:
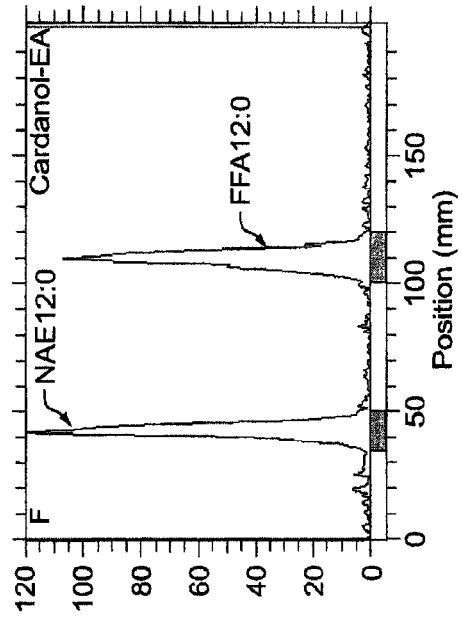
Figure 4E:
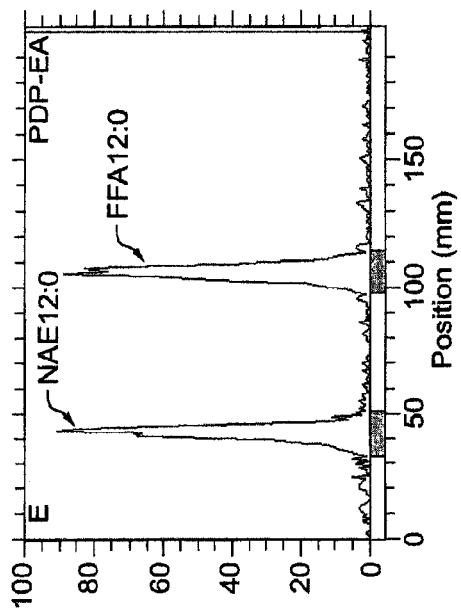
Figure 4G:
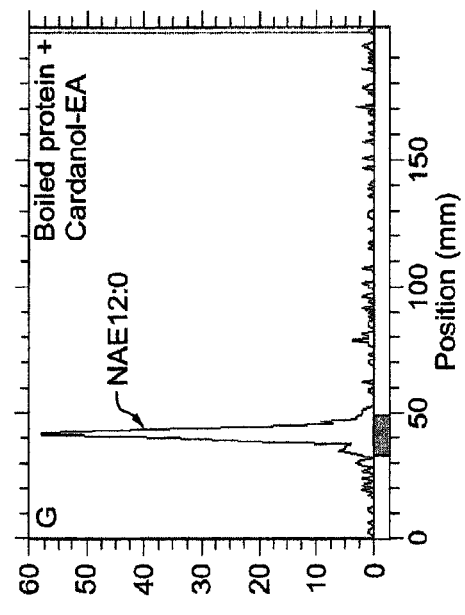
Figure 5B:
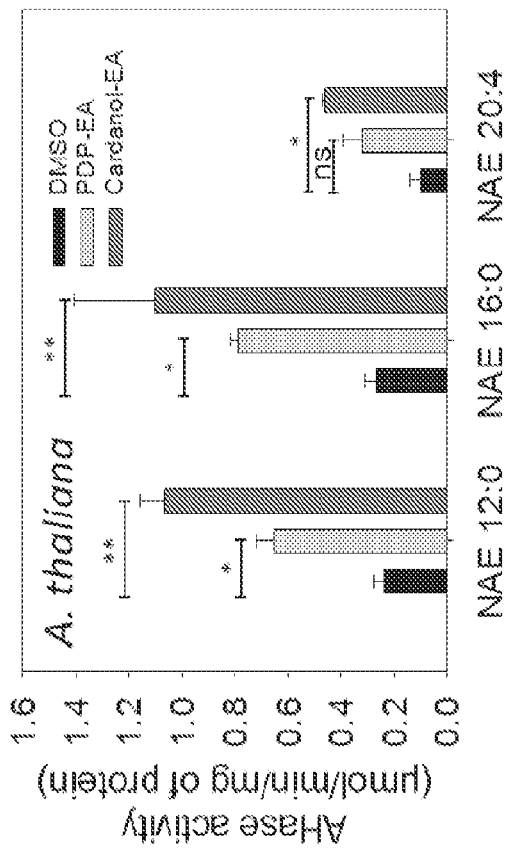
Figure 5A:
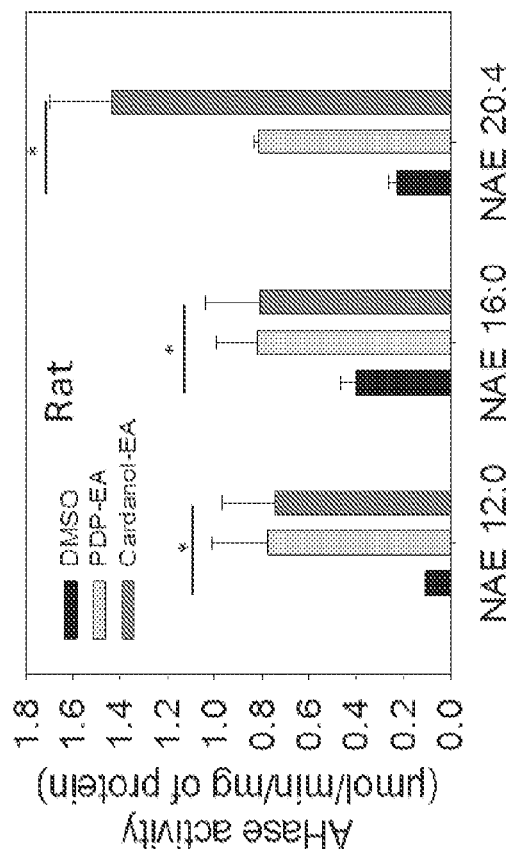

To test whether these phenoxyacyl-ethanolamide might serve as inhibitors of NAE hydrolysis by the FAAH enzymes, we measured the hydrolysis of 100 μM of [1-$^{14}$C]-NAE 12:0 with or without 100 μM of PDP-EA or cardanol-EA. Instead of reductions in FAAH activity as expected, the amidohydrolase activity of both FAAH enzymes toward NAE was increased in presence of either phenoxyacyl-ethanolamide compound (FIG. 4A to 4G). Non-enzymatic hydrolysis of NAE to free fatty acid by PDP-EA or cardanol-EA could be ruled out since no activity was measured in assays using heat-denatured enzyme (FIG. 4G). FAAH activities toward different NAEs, such as [1-$^{14}$C]-N-palmitoylethanolamine (NAE 16:0) or [1-$^{14}$C]-N-arachidonoylethanolamine (NAE 20:4, anandamide) showed a similar enhancement in the presence of the new NAE-like compounds (FIG. 5A and FIG. 5B). An increase of activity by a factor of about 4±1.2 for the recombinant At-FAAH protein was measured in presence of either PDP-EA or cardanol-EA and by a factor of about 5±2.2 for the rat FAAH protein for the unsaturated NAE (NAE 16:0 and NAE 12:0), and up to a factor 7±1.1 for the rat FAAH protein and NAE 20:4 (FIG. 5A and FIG. 5B).

Kinetic Parameters of At- and Rat FAAH Proteins—

Each enzyme exhibited typical Michaelis-Menten-type kinetics when initial velocity measurements were made at increasing concentrations of NAE 12:0 or NAE 20:4 substrates for At-FAAH or rat FAAH, respectively. Both apparent $V_{max}$ ($V_{max}^{app}$) and apparent $K_m$ ($K_m^{app}$) were calculated for each enzyme and summarized (FIG. 6A, FIG. 6B, FIG. 6C). No statistical difference (T-test, confidence level 95%) for the $K_m^{app}$ values of the At-FAAH was observed with or without 100 μM of either PDP-EA or cardanol-EA (FIG. 6A, FIG. 6B, FIG. 6C). However, catalytic efficiency ($K_{cat}/K_m$) of the At-FAAH enzyme increased in presence of both phenoxyacyl-ethanolamides ($9.8×10^4 M^{-1}/s^{-1}$ or $1.58×10^5 M^{-1}/s^{-1}$ compared with solvent control of $3.8×10^4 M^{-1}/s^{-1}$). The $K_m^{app}$ obtained in our assays for the plant FAAH was similar to $K_m$ values determined elsewhere (17.6 μM).

For the rat FAAH, there was an increase by a factor of about 3 of the rat $K_m$ estimated in presence of both phenoxyacyl-ethanolamides compounds (173±18–179±25 μM) compared to that measured in solvent controls (56±7.07 μM). Similar to At-FAAH, rat FAAH exhibited an increase in $K_{cat}$ in the presence of PDP-EA and cardanol-EA, indicating an increase in turnover rate of the recombinant protein with respect to NAE. However, similar values of the ratio $K_{cat}/K_m$ were calculated for the rat FAAH with or without the phenoxyacyl-ethanolamides (due to reduced affinity of the enzyme for the NAE substrate), suggesting a similar catalytic efficiency of the rat enzyme with or without these compounds. Although there is variation in reported kinetic parameters for rat FAAH, those measured here were similar to those reported elsewhere.

Protection by Phenoxyacyl-Ethanolamides from Ethanolamine Product Inhibition for Both At- and Rat FAAH—

Figure 7A:
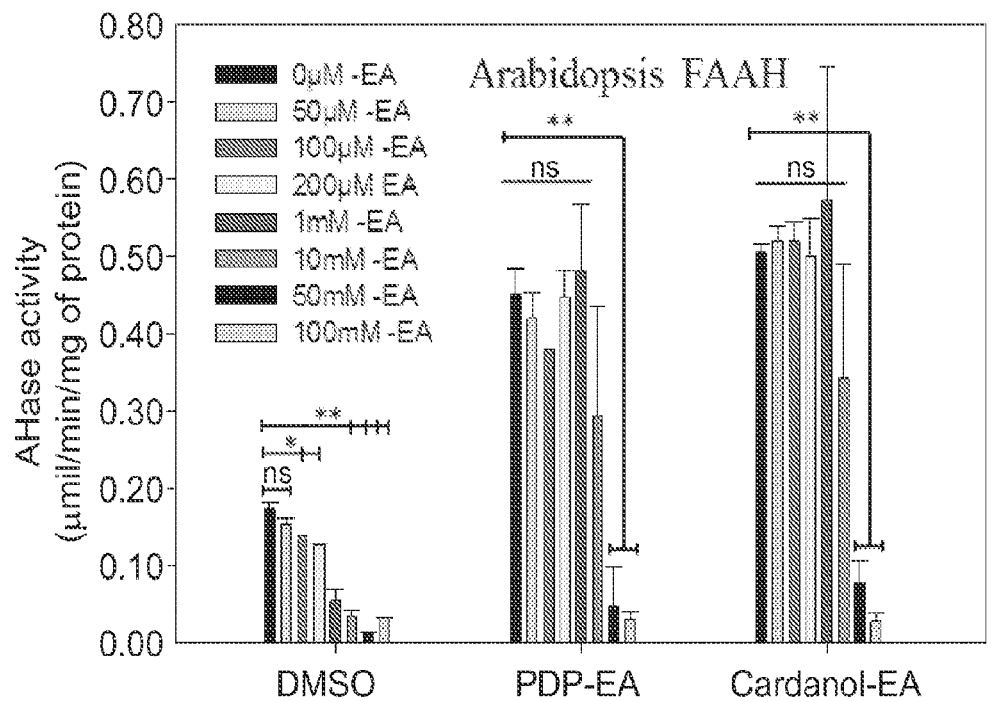
FIGS. 7A and 7B show inhibition of At-FAAH1 or rat FAAH proteins at increasing concentrations of ethanolamine (EA) and protection from inhibition by 100 μM of PDP-EA or cardanol-EA. Reactions were initiated by the addition of 0.3 μg of At-FAAH (FIG. 7A) or with rat FAAH (FIG. 7B) purified proteins. Reactions were carried out in 50 mM BisTris propane-HCl (pH 9.0), 0.2 mM DDM at 30° C. with 100 μM of [1-$^{14}$C]-NAE 12:0 in a final volume of 0.15 ml. Data points represent means±S.D. of triplicate assays. Plots were generated with SigmaPlot software version 12.0.
Figure 7B:
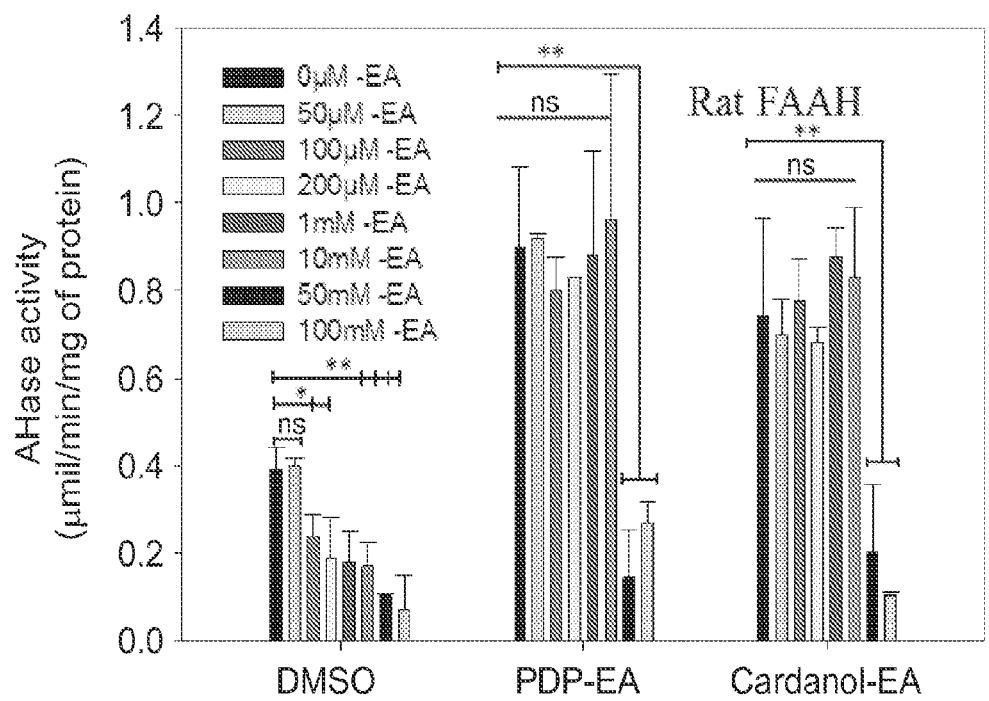

We noted a statistical dose-dependent reduction in NAE hydrolase activity at increasing ethanolamine concentrations (FIG. 7A and FIG. 7B). While enzyme regulation by product inhibition is not uncommon, feedback inhibition of FAAH by ethanolamine has not been described neither for rat nor for At-FAAH. We demonstrated that this regulatory feature is evident for both At-FAAH and rat FAAH. Perhaps even more interesting, both PDP-EA and cardanol-EA relieved this ethanolamine inhibition almost completely at concentrations up to 10 mM ethanolamine (FIG. 7A and FIG. 7B). No dramatic change in pH of the reaction was measured following the addition of ethanolamine (-up to 10 mM, pH 9.0; at 100 mM, pH 9.7; 25° C.), indicating the inhibitory effects of ethanolamine were not due to alterations in reaction pH.

Effects of PDP-EA and Cardanol-EA on Plant Growth—

Figure 8:
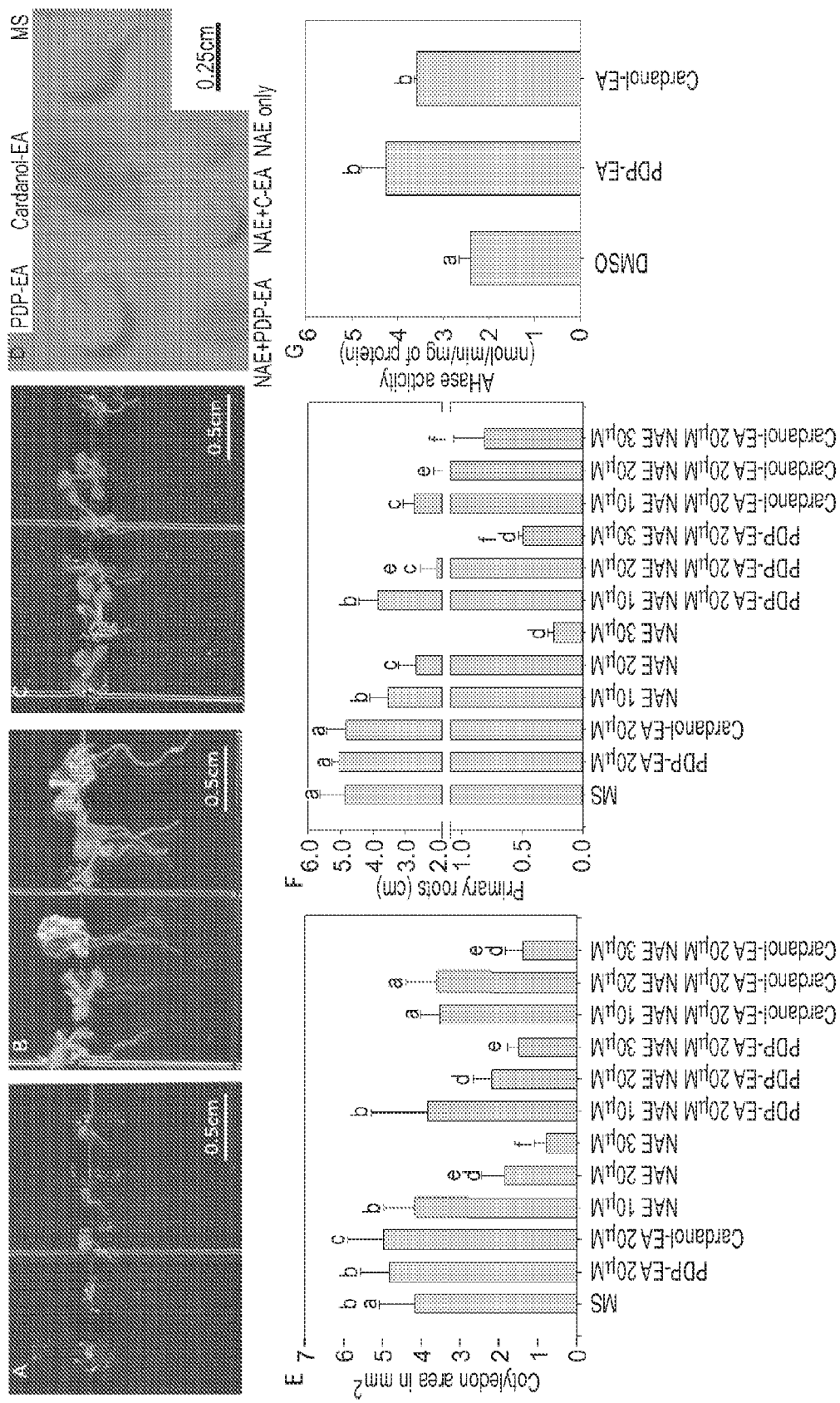
FIG. 8 illustrates a characterization of NAE sensitivity and NAE amidohydrolase activity for *Arabidopsis* seedlings in the presence or absence of PDP-EA or cardanol-EA; panel A, *Arabidopsis thaliana* wild type (Col-0) seedlings with 30 μM NAE 12:0; panel B, Seedlings plus 30 μM NAE 12:0 and 20 μM cardanol-EA; panel C, Seedlings plus 30 μM NAE 12:0 and 20 μM PDP-EA, panel D, images of the cotyledon sizes of seedlings in presence of 20 μM of phenoxyacyl-ethanolamide compounds+/−30 μM of NAE 12:0; seedlings were grown with these different treatments for 11 days under long day conditions. panel E and panel F, show the sizes of the cotyledons or roots as a function of different NAE, PDP-EA or cardanol-EA concentrations. panel G, FAAH activity, reactions were initiated by the addition of 6 μg of crude plant protein extract from 11-d-old seedlings in 50 mM BisTris propane-HCl (pH 9.0), 0.2 mM DDM at 30° C. for 2 hours with 200 μM of [1-$^{14}$C]-NAE 12:0 and 200 μM of NAE-like compounds in a final volume of 0.3 ml; data points represent means±S.D. of triplicate assays; plots were generated with SigmaPlot software version 12.0. N+C-EA (NAE 12:0+cardanol-EA); means with different letters are significantly different (P<0.005) determined by one-way ANOVA with Tukey's post-test.

Negative effects on seedling growth by exogenous NAE 12:0 are well documented. PDP-EA and cardanol-EA were able to reverse partially these negative growth effects (FIG. 8). Representative images of *Arabidopsis* seedlings germinated and grown in media containing NAE 12:0 alone, or NAE 12:0 with PDP-EA or cardanol-EA, are shown in FIG. 8 (panels A-C). Quantitative measurements of seedling growth (cotyledon size and primary root elongation) are summarized in FIG. 8, panels E and F. Despite a somewhat similar structure to NAE 12:0, PDP-EA alone, and especially cardanol-EA alone, showed a positive impact on seedling growth (cotyledon size, FIG. 8, panels D, E) opposite to the effects of NAE 12:0. And both compounds partially reversed the negative effects of NAE 12:0 with respect to cotyledon size. Cardanol-EA reversed negative growth effects of NAE 12:0 in primary roots. One potential explanation for these effects on seedling growth by PDP-EA and cardanol-EA is through their biochemical enhancement of At-FAAH activity in vivo. FAAH overexpression in transgenic *Arabidopsis* (with increased FAAH activity) conferred enhanced seedling growth as well as tolerance of the negative growth effects of NAE, with effects on cotyledon size and primary root length very similar to those observed here by adding these phenoxyacyl-ethanolamides to non-transgenic seedlings (FIG. 8). As expected, NAE amidohydrolase activity from crude seedling extracts showed an enhancement when assayed in the presence of PDP-EA or cardanol-EA and [1-$^{14}$C]-NAE 12:0 (FIG. 8, panel G). Therefore, it is possible that exogenous application of these phenoxyacyl-ethanolamides can stimulate FAAH activity in planta and positively influences plant growth.

Effects of Cardanol-EA on Viability of Cultured Primary Neurons—

Figure 9A:
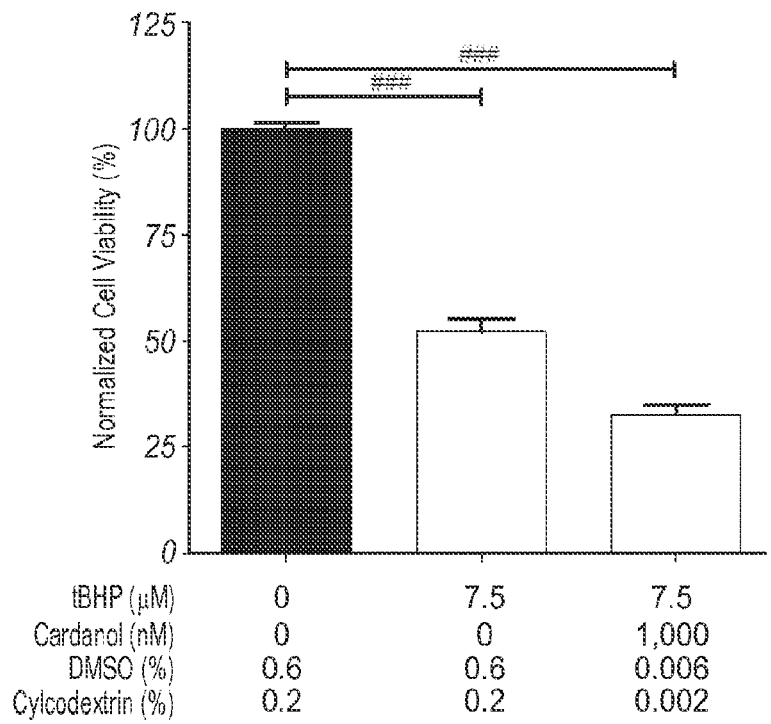
FIGS. 9A, 9B, 9C and 9D are cardanol-EA pre-treatment sensitizes primary cortical neurons to oxidative insult in a FAAH-dependent manner; rat E18 cortical neurons were pre-treated for 1-2 hours with cardanol-EA prior to an overnight (16-18 hour) tBHP exposure; the cardanol-EA stock solution was pre-diluted 1:5 in 2-hydroxypropyl-β-cyclodextrin prior to dilution in media to enhance delivery; neuronal viability was measured by calcein fluorescence and normalized to the vehicle control.
Figure 9B:
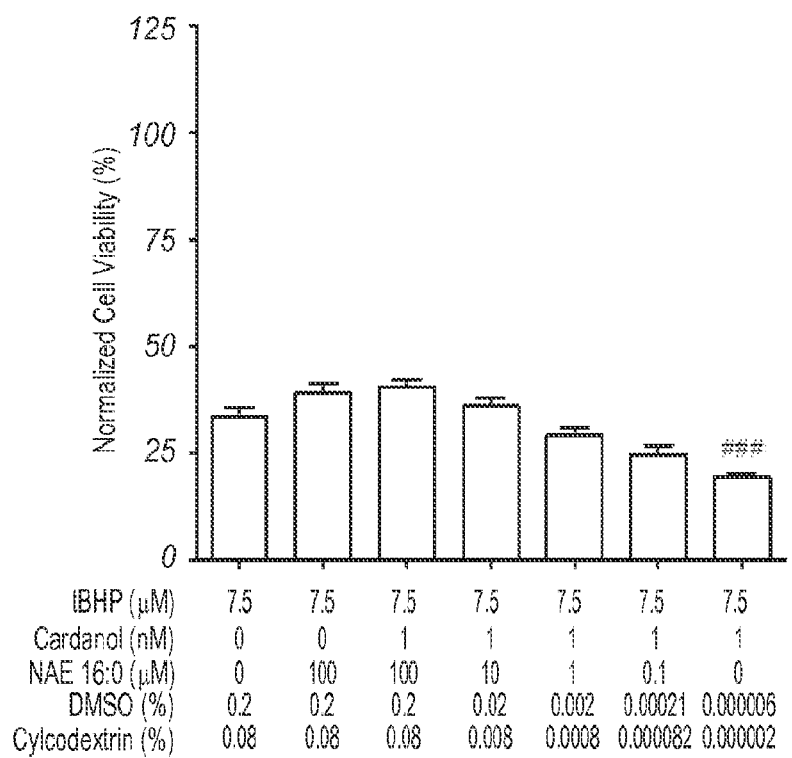
Figure 9C:
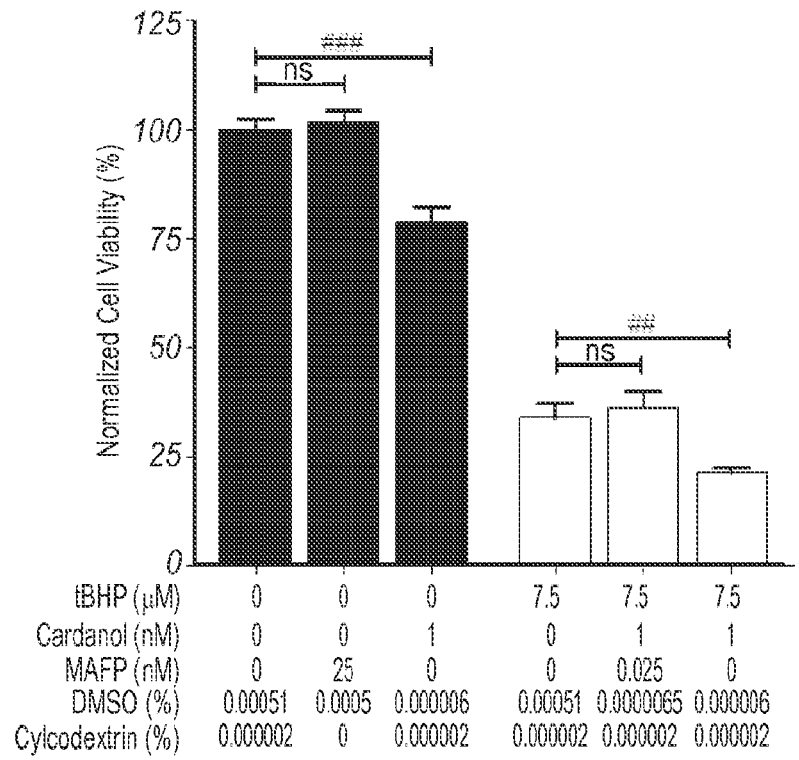
Figure 9D:
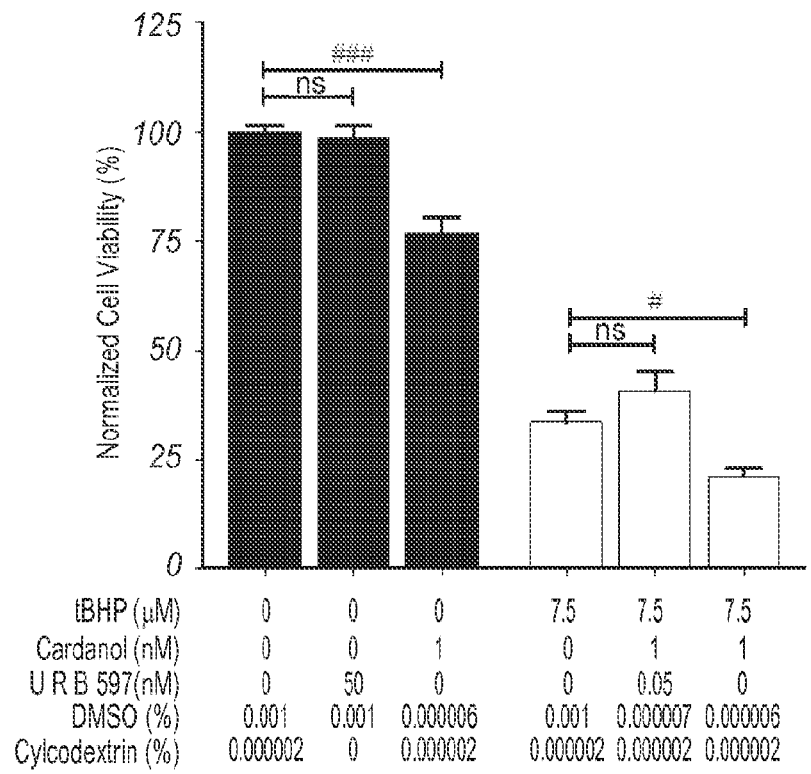

Treatment of cultured embryonic primary neurons with cardanol-EA exacerbated tert-butyl hydroperoxide-mediated (tBHP) cell death (FIG. 9A-D). Following overnight exposure to oxidative stress induced by treatment with 7.5 µM tBHP, neuronal cultures pre-treated with 1 µM cardanol-EA contained 18% fewer viable cells than cultures pre-treated with vehicle alone (FIG. 9A). Incubation of neurons with the exogenously administered FAAH substrate, NAE 16:0 (N-palmitoylethanolamine) for 1 hour prior to addition of 1 nM cardanol-EA resulted in a dose-dependent reversal of cardanol-induced exacerbation of tBHP mediated cell death (FIG. 9B). Primary neurons treated with cardanol-EA and incubated in anti-oxidant free media overnight demonstrated a significant reduction in viability compared to neurons incubated overnight in anti-oxidant free media with vehicle or with the specific, irreversible, FAAH inhibitors MAFP and URB597 (FIG. 9C and FIG. 9D, respectively). Incubation of neurons with these inhibitors for one hour prior to the addition of cardanol-EA completely reversed cardanol-induced exacerbation of tBHP mediated cell death, suggesting that this ex vivo effect of cardanol-EA is a result of FAAH activation.

Despite the structural similarity between the phenoxyacyl-ethanolamide compounds synthesized for these studies (FIG. 1A) and the naturally occurring NAE lipids that are present in essentially all multicellular eukaryotes, neither of the FAAH proteins (rat or *Arabidopsis*) were able, in our conditions, to utilize these compounds efficiently as substrates for hydrolysis (FIG. 3). This was somewhat surprising given the broad range of acyl amides and acyl esters that can be hydrolyzed by FAAH. On the other hand, previous studies demonstrated that substitutions at the α-position of the acyl chain of primary amide or anandamide analogues compounds rendered the compound resistant to hydrolysis by FAAH. The incorporation of a bulky phenoxy-group near the amide moiety may serve a similar structural hindrance to the enzyme's active site and restrict hydrolysis. However, even if these newly synthesized lipids were not used as substrates by FAAH, we speculated that these compounds would act as inhibitors toward NAE hydrolysis. Instead, a rather unique characteristic was identified for these compounds; we found that these phenoxyacyl-ethanolamides functioned to stimulate hydrolysis of NAEs by FAAH (FIGS. 4A to 4G, FIGS. 5A and 5B, FIGS. 6A, 6B, and 6C). These compounds stimulated the activity of FAAH from both plant and mammalian sources, suggesting a more general feature of FAAH, not specific to the type of organism. There were subtle differences between plant and mammalian FAAH, such as the impact of the phenoxyacyl-ethanolamides on the affinity of the enzyme toward NAEs (raised the $K_m$ for NAE 20:4 in rat FAAH substantially, but did not statistically (T-test, confidence level 95%) affect the $K_m$ for At-FAAH). On the other hand, in both plant and mammalian FAAH, the turnover number of the enzyme was increased by addition of the phenoxyacyl-ethanolamides (FIGS. 6A to 6C). Moreover, a new negative feedback property of FAAH activity by ethanolamine was discovered for both FAAH proteins and this was prevented to a substantial degree by the addition of the phenoxyacyl-ethanolamides (FIGS. 7A and 7B).

The detergent Triton X-100 has been used extensively for the solubilization and to enhance the recoverable activity of recombinant rat FAAH. This non-ionic detergent likely mimics somewhat the endogenous membrane environment of FAAH and maintains the functional amidase and esterase activities of the enzyme toward lipophilic substrates. In the case of At-FAAH, Triton X-100 appeared to be better than the alkylglycoside detergent, DDM, (FIG. 2C) historically used for solubilizing active At-FAAH enzyme. However, $K_m$ values measured here were generally similar for At-FAAH solubilized in DDM (26±5.09 µM FIG. 6C vs. 13-50 µM in previous studies), and this procedural change allowed for more consistent comparisons between plant and animal FAAH enzymes for our comparative studies. Even so, both PDP-EA and cardanol-EA enhanced FAAH activities from both plant and animal sources (FIGS. 4, 5A, 5B, 6A, 6B and 6C), and prevented product inhibition by ethanolamine at least up to 10 mM (FIGS. 7A and 7B). The increase in FAAH turnover number measured in FIGS. 6A to 6C in the presence of phenoxyacyl-ethanolamides may be a direct result of prevention of product inhibition by ethanolamine, even in the case of rat FAAH where the affinity for NAE substrate appeared to be reduced by the phenoxyacyl-ethanolamide analogues. It still remains to be clarified directly whether the effect of the phenoxyacyl-ethanolamides is via a specific binding site on FAAH or is more general in terms of influencing FAAH or substrate solubility. However, the effects of these compounds on NAE-mediated inhibition of seedling growth or in the modulation of neuronal cell death would suggest that these compounds indeed act through a specific effect on the FAAH enzyme per se.

NAE 12:0 inhibits seedling growth when applied exogenously (see FIG. 8, and also references). Co-application of PDP-EA and especially cardanol-EA reversed these inhibitory growth effects of NAE 12:0 (FIG. 8). Similarly, the overexpression of FAAH in transgenic *Arabidopsis* seedlings also results in an NAE tolerant phenotype. It is possible that the new phenoxyacyl-ethanolamides are able to enhance endogenous FAAH activity in wild-type seedlings, to confer some tolerance to the growth inhibition by NAE 12:0. Certainly there are other possible mechanisms by which these phenoxyacyl-ethanolamides might be acting, and this area will require further experimentation, but to date, only increased activity of FAAH has been shown to confer tolerance toward NAE 12:0, and this is consistent with the in vitro action of PDP-EA and cardanol-EA on purified recombinant FAAH enzymes (FIGS. 4-7B), and in crude seedling homogenates (FIG. 8, panel G).

One intriguing aspect of these compounds is their growth promoting properties in seedlings (FIG. 8). This is especially evident for cardanol-EA and its influence on cotyledon size (FIG. 8, panels D and F). This is exactly the opposite effect of NAEs which appear to retard growth and reduce cotyledon size. Besides their antagonistic effects on NAE treatment in seedlings, it seems that these compounds have their own inherent growth regulating properties. Interestingly, seedlings overexpressing FAAH showed significant increases in cotyledon size (and other organs as well), again suggesting that these phenoxyacyl-ethanolamides may be acting through modulation of endogenous FAAH activity.

The cardanol-EA-mediated reduction of cellular viability and exacerbation of oxidative stress induced cell death in primary neurons (FIGS. 9A, 9B, 9C and 9D) are potentially mediated by the depletion of neuroprotective NAEs through an increase of FAAH activity (FIGS. 5A and 5B). The reversal of cardanol's sensitizing effect on neuronal cell death by NAE 16:0 begins well below its reported $IC_{50}$ of 5.1 µM for anandamide hydrolysis by rat brain FAAH, which may indicate that cardanol-EA does not affect binding of NAE 16:0 to rat FAAH in the same way that it does with anandamide (3.1 fold increase in $K_m$; FIG. 6A to 6C). The specificity of the pharmacological inhibitors of FAAH used to reverse cardanol-induced exacerbation of tBHP mediated cell death (FIG. 9C and FIG. 9D), suggest FAAH activation as the underlying mechanism of action.

Figure 1B:
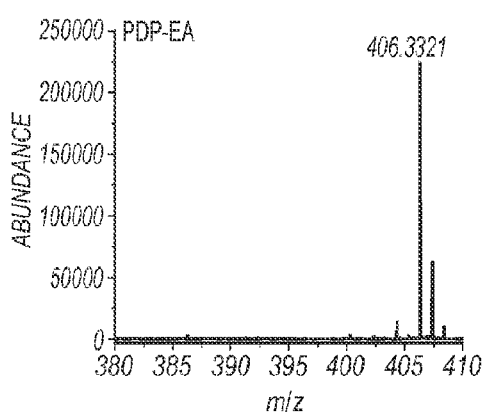
FIGS. 1B and 1C are high-resolution mass spectrometry (HRMS) for phenoxyacyl-ethanolamides (a) 3-N-pentadecylphenolethanolamine ($[M+H]^+$=m/z 406.3321 and its $^{13}C$ isotopic peak $[M+H]^+$=m/z 407.3362); (b) cardanol-ethanolamide (with three unsaturation: $[M+H]^+$=m/z 400.2845 and its $^{13}C$ isotopic peak $[M+H]^+$=m/z 401.2881 with two unsaturation: $[M+H]^+$=m/z 402.2996 and its $^{13}C$ isotopic peak $[M+H]^+$=m/z 403.3030; with single unsaturation: ($[M+H]^+$=m/z 404.3163 and its $^{13}C$ isotopic peak $[M+H]^+$=m/z 405.3199; saturated: ($[M+H]^+$=m/z 406.3297 and its $^{13}C$ isotopic peak $[M+H]^+$=m/z 407.3332)
Figure 1C:
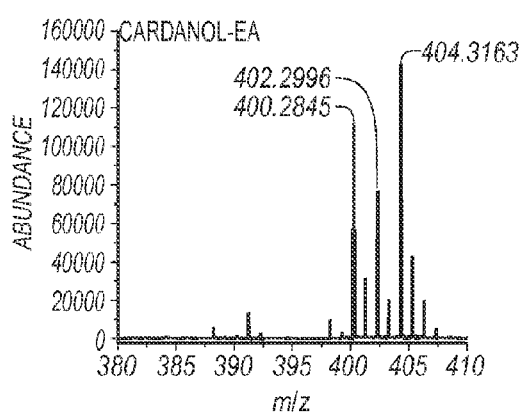

Cardanol-EA is a mixture of different phenoxyacyl-ethanolamides all with fifteen carbon alkyl chains (FIGS. 1A, 1B and 1C). Fifty percent of this mixture is composed of an alkyl chain with one double bond, 16% with two double bonds, 29% with three double bonds and with 5% of PDP-EA with no double bonds (saturated form). The PDP-EA compound is a single species with a fifteen carbon saturated alkyl chain. There may be some slight differences in terms of action on FAAH between the two phenoxyacyl-ethanolamide preparations, but generally, the stimulatory activity was observed for both compounds. The advantage of the cardanol-EA mixture is that it is synthesized from natural materials found in many plant sources. The starting materials for these phenoxyacyl-ethanolamides are derived from cardanol, which are major constituents of cashew nut shell waste streams, and ethanolamides synthesized from these phenolic lipids may find many applications beyond their chemical properties as lipophilic hydrocarbon polymers. Given the plant growth promoting properties, especially of cardanol-EA, there may be agricultural applications for these compounds. Or based on their action on FAAH activity, these compounds may find therapeutic applications where manipulation of localized endogenous NAE levels might be desired.

Overall, the activities of these two new NAE-like compounds (PDP-EA and cardanol-EA) open a new interesting and unexplored approach for the in situ regulation of NAE metabolism in plant and animal systems. For example these molecules might be used as pharmacological agents to modulate appetite by decreasing the endogenous levels of acylethanolamide agonists in animal systems, as chemosensitizing agents targeted at lipid signaling pathways affected by disease processes or as a modulator of endocannabinoid signaling in applications ranging from cytoprotection, to cellular development and excitable cell function. In plants, NAE metabolism has been shown to be associated with biotic and abiotic stresses as well as seedling and reproductive growth and development. Hence, these compounds might find applications in agriculture. Further experiments will need to be done to define utility of these FAAH enhancers in vivo to modulate the numerous effects of NAEs in plants and animals.

EXPERIMENTAL PROCEDURES

Materials—

$[1-^{14}C]$-Lauric acid was from Amersham Biosciences, $[1-^{14}C]$-palmitic acid was purchased from NEN (Boston Mass.), and $[1-^{14}C]$-arachidonic acid was purchased from PerkinElmer Life Sciences. Ethanolamine, anandamide, isopropyl-β-D-thiogalactopyranoside (IPTG), Triton X-100 were from Sigma Chemical Co (St. Louis). N-dodecyl-β-D-maltoside (DDM) was from Calbiochem (LA Jolla, Calif.). Sprague/Dawley rat E18 cortical neurons, NeuroPapain, NeuroPrep medium, and NeuroPure plating medium were obtained from Genlantis (San Diego, Calif.). Neurobasal media, B27 supplement, B27 antioxidant-free supplement, GlutaMAX I, and calcein-AM were purchased from Invitrogen. BD PureCoae™ amine plates were obtained from BD Biosciences. DMSO and 2-hydroxypropyl-β-cyclodextrin were purchased from Sigma Chemical Co. (St. Louis, Mo.). tert-butyl hydroperoxide (tBHP) was obtained from Acros Organics (part of Thermo Fisher Scientific, New Jersey). PBS and penicillin/streptomycin were purchased from Lonza (Walkersville, Md.). Palmitoylethanolamide was from Best West Laboratories (Salt Lake City, Utah), MAFP was from Tocris Biosciences, and URB597 was from EMD Millipore. Silica Gel G (60 A)-coated glass plates for thin-layer chromatography (10 cm×20 cm or 20 cm×20 cm, 0.25 mm thickness) were from Whatman (Clifton, N.J.). Different species of N-$[1-^{14}C]$-acylethanolamines (and non-radiolabeled NAEs) were synthesized from ethanolamine and corresponding $[1-^{14}C]$-fatty acids (and non-radiolabeled FFAs) by first producing the fatty acid chloride and purifying by thin layer chromatography (TLC) as described elsewhere. The chemical compounds PDP-EA and cardanol-EA were produced as described below.

Synthesis of 3-N-Pentadecyl-Ethanolamide (PDP-EA) and the More General Mixed Species Cardanol-Ethanolamide (Cardanol-EA)—

For the cardanol-EA: In a round bottom flask fixed with magnetic stirrer, cardanol-methyl ester (3.74 g, 10 mmol) was added, followed by dichloromethane (DCM) (25 mL) and Triethylamine (TEA) (1.4 mL, 10 mmol). Reaction mixture was stirred for 2 minutes, followed by the drop wise addition of ethanolamine (0.66 mL, 11 mmol) in an ice bath with constant stirring. The resultant mixture was stirred at room temperature for about 6-8 h. After the completion of reaction, as identified using TLC, ice cold water was added and the lipids extracted with ethyl acetate. The organic phase was separated and dried over anhydrous sodium sulfate, filtered, and concentrated. Pure product as a colorless liquid was obtained by column chromatographic purification. At 5° C., the viscous liquid solidifies in to pale yellow solid. Yield=78%. $^1$H NMR (CDCl$_3$, 300 MHz): δ 7.17 (s, 2H), 6.68-6.83 (m, 3H), 5.36 (d, 3H), 4.45 (s, 2H), 3.72 (s, 2H), 3.49 (s, 3H), 2.78 (s, 1H), 2.56 (d, 2H), 2.14 (s, 1H), 2.01 (s, 2H), 0.86-1.57 (m, 20H); $^{13}$C NMR (CDCl$_3$, 75 MHz): δ 169.91, 157.33, 145.25, 130.28, 130.15, 130.00, 129.68, 122.58, 122.43, 115.18, 114.99, 111.88, 111.69, 67.36, 61.85, 42.04, 36.15, 31.99, 31.59, 29.93, 29.45, 29.41, 22.89, 14.33. High-resolution MS analysis showed [M+H]$^+$, m/z 404.3163 (for the principal ethanolamide species in the cardanol-EA preparation) compared to the calculated mass for $C_{25}H_{41}NO_3$, [M+H]$^+$ of m/z 404.3165. To synthesize and purify the PDP-EA [N-(2-hydroxyethyl)-2-(3-entadecylphenoxy) acetamide], a similar scheme was used as for cardanol EA, except pure PDP methyl ester was used to generate the acylethanolamide. Purity of crude product was greater than 90%. Pure PDP-EA product, as colorless crystals, was obtained by column chromatographic purification. Yield=92%. $^1$H NMR (CDCl$_3$, 300 MHz): δ 7.18 (s, 2H), 6.84 (s, 1H), 6.73 (s, 2H), 4.77 (s, 1H), 4.47 (s, 2H), 4.11 (s, 1H), 3.72 (s, 2H), 3.45 (s, 2H), 2.56 (s, 2H), 2.02 (s, 1H), 1.57 (s, 2H), 1.25 (s, 22H), 0.87 (s, 3H); $^{13}$C NMR (CDCl$_3$, 75 MHz): δ 169.76, 157.29, 145.35, 129.72, 122.66, 115.20, 114.91, 111.89, 67.34, 62.18, 42.12, 36.16, 32.13, 31.61, 29.89, 22.91, 14.48. High resolution MS analysis of the PDP-EA matched exactly with the calculated mass for $C_{25}H_{43}NO_3$, [M+H]$^+$ of m/z 406.3321.

Plant Material and Cultures—

Ten mg *Arabidopsis thaliana* (ecotype Col-0) seeds were surface sterilized and then stratified in the dark for 2 days at 4° C. prior to sowing in liquid (75 ml) or solid Murashige and Skoog (MS) medium (14). Growth of seedlings was in 16 h-light/8 h-dark cycle (60 μmol·m$^{-2}$·s$^{-1}$) for 11 days at 20° C.

Plasmid Constructs—

The recombinant plasmid, rat FAAH1-pTrcHis2 (NCB Accession # NP_077046), was provided by Dr Benjamin Cravatt's laboratory (34) and the plasmid At-FAAH-pTrcHis2 (At5g64440, UniProt # Q7XJJ7) was constructed as described in prior studies. The expression constructs were introduced into chemically competent *E. coli* TOP10 cells as host as described in the manufacturer's instructions.

Protein Expression and Solubilization for Enzymatic Assays—

The different cell lines were grown in 250 ml of LB medium with 100 μg·ml$^{-1}$ of filtered ampicillin to an $A_{600}$ of 0.6 and induced with 1 mM IPTG for 4 hours at 37° C. Each culture was centrifuged at 5000 rpm for 10 minutes at 4° C. in a Beckman tabletop centrifuge (rotor, GH 3.7). The pelleted cells expressing rat FAAH1 or At-FAAH1 were resuspended in 10 ml of lysis buffer A (50 mM Tris-HCl, pH 8.0, 100 mM NaCl, 1% TritonX-100) or 10 ml of lysis buffer B (50 mM Tris-HCl, pH 8.0, 100 mM NaCl, 0.2 mM DDM). After incubation on ice for 30 min, resuspended cells were sonicated on ice with ten, 30-sec burst at 50% intensity with 30-sec cooling (ice) period between bursts. Each crude lysate was centrifuged at 13,000×g for 20 min at 4° C. in a Sorvall RC 5C model ultracentrifuge (Sorvall rotor, SS-34). The supernatant was applied to a QIQIEXPRESS® NI-NTA Fast Start (QIAGEN®) column and the proteins were purified according to the manufacturer's instructions. The purified fractions (2 ml) were concentrated, and imidazole was removed with buffer C (50 mM Bis-Tris propane-HCl, pH 9.0, 0.2 mM DDM) by filtration-centrifugation using Centricon YM-30 (Millipore, Bedford, Mass.) devices. The protein concentration was estimated by Bradford reagent (Sigma; St. Louis; MO) against a BSA standard curve, and the purity of the proteins was evaluated by SDS-PAGE gel and western blotting. The rat or At-FAAH proteins were aliquoted (20 μl) and stored at −80° C. up to several months and thawed once for use.

Plant Protein Extraction—

After 11 days in liquid culture the plant material was rinsed with milliQ water and then blotted dry. With a mortar and pestle the plant material (500 mg) was ground with liquid nitrogen and then with 2 ml of plant protein solubilization solution (0.1 M potassium phosphate buffer, pH 7.2, 400 mM sucrose, 10 mM KCl, 1 mM EDTA, 1 mM EGTA, 1 mM MgCl$_2$) with 0.2 mM of DDM. The crude extract was vortexed (full power) for 1 min then incubated at 4° C. for 30 min with regular shakes. The crude extract was centrifuged at 2000 rpm at 4° C. for 10 min in a Beckman (rotor, GH 3.7). The supernatant, containing the total solubilized proteins, was stored at 4° C. up to 2 days.

SDS-PAGE and Western Blotting—

Each aliquot (rat or At-FAAH protein) was separated by SDS-PAGE (10% resolving gels) according to Shrestha, R., Dixon, R., and Chapman, K. (2003) Molecular identification of a functional homologue of the mammalian fatty acid amide hydrolase in *Arabidopsis thaliana*. *Journal of Biological Chemistry* 278, 34990-34997. The proteins were visualized in gels by Coomassie-blue staining, or proteins were electrophoreticly transferred to polyvinylidene fluoride (PVDF) membranes (0.2 μm, Bio-Rad, Hercules, Calif.) according to the protocol described elsewhere (10). The recombinant proteins expressing the HIS tag at the C-terminus were detected by chemiluminescence using a 1-to-2000 dilution of mouse monoclonal anti-HIS antibodies (ABGENT San Diego, Calif.) and a solution of 1-to-4000 dilution of goat anti-mouse IgG conjugated to a peroxidase (Bio-Rad).

FAAH Assays on Purified Proteins—

The NAE amidohydrolase assays were conducted as previously described by Shrestha et al and others with few modifications. The reactions were conducted for 30 min at 30° C., in 150 μl of buffer C containing different concentrations of radiolabelled NAEs, the new NAE-like compounds and different concentrations of purified protein (see legends of figures for more details in the composition of each reaction mixture). Enzyme reactions were terminated by the addition of hot isopropanol (70° C.). The lipids were extracted and the distribution of the radioactivity was evaluated by radiometric scanning of TLC plates as described in Shrestha, R., Kim, S, Dyer, J., Dixon, R., and Chapman, K. (2006) Plant fatty acid (ethanol) amide hydrolases. *Biochimica Et Biophysica Acta-Molecular and Cell Biology of Lipids* 1761, 324-334.

Plant Amidohydrolase Assays—

The reactions were conducted at 30° C. for 2 hours in buffer C with 300 μM of PDP-EA or cardanol-EA and 200 μM of radiolabeled NAE 12:0. Reactions were initiated by adding 5 μg of total protein and terminated by the addition of hot isopropanol. Lipids were extracted and analyzed as above.

Ethanolamine Inhibition Assays—

Assays containing 0.3 μg purified FAAH protein were first incubated with 100 μM of PDP-EA or cardanol-EA and then with different concentrations of ethanolamine (0-100 mM) (Vf=150 μl of buffer C). Reactions were initiated by adding 100 μM of radiolabeled NAE and terminated as described. The lipids were extracted and the total distribution of the radioactivity was calculated as above.

Primary Neuronal Culture—

Commercially obtained Sprague/Dawley rat E18 cortical tissue was allowed to settle for 5-10 minutes at room temperature, the shipping media was removed (reserved at 37° C.), and the tissue was enzymatically treated with NeuroPapain dissolved in NeuroPrep Medium (2 mg/ml, 2.5 ml) for 28 minutes at 37° C. with gentle swirling every 7 minutes. Treated tissue was centrifuged for 1.5 minutes at 200×g and the cells were dissociated by gentle trituration in 1 ml of the reserved shipping medium. Cells were collected by centrifugation as above and re-suspended by gentle trituration in 1 ml of NeuroPure plating medium. Viable cells were counted, (Nexcelom Auto T4; Nexcelom Bioscience LLC. Lawrence, Mass.) re-suspended in 9 ml of NeuroPure plating medium plus enough Neurobasal medium (supplemented with B27; GlutaMAX I, 2 mM; Penicillin, 50 U/ml; Streptomycin, 50 μg/ml) to achieve a density of 250,000 cells/ml, and seeded in BD PureCoat™ black-walled amine-coated 96-well plates in a 100 μl volume. Cultures were maintained at 37° C., 5% $CO_2$, 95% humidity for 7 days prior to experiments with a 50% media exchange on day 3.

Effects of Cardanol-EA on Cultured Primary Neurons—

One hundred millimolar of cardanol-EA in DMSO was diluted 1:5 in warm 40% 2-hydroxypropyl-β-cyclodextrin dissolved in DMSO and incubated for 10 minutes at 50° C. prior to serial dilution in warm Neurobasal media containing antioxidant-free B27 supplement, GlutaMAX I (2 mM), penicillin (50 U/ml), and streptomycin (50 µg/ml). Growth media was exchanged for 100 µl antioxidant-free media containing serial dilutions of cardanol-EA or vehicle (0.6% DMSO, 0.2% 2-hydroxypropyl-β-cyclodextrin) and plates were incubated as above for 1-2 hours. Oxidative stress was induced by the addition of concentrated tert-butyl hydrogen peroxide (tBHP) to achieve a final concentration of 7.5 µM. Controls were treated with an equivalent volume of PBS. After 16-18 hours, the cell culture medium was replaced with 100 µl pre-warmed PBS containing 5 µg/ml calcein-AM and plates were returned to the incubator for 30 minutes. Cell viability was determined by measuring calcein fluorescence on a FlexStation3 plate reader (Molecular Devices, Sunnyvale, Calif.) at 485/525 nm excitation/emission with a 515 nm emission cutoff, subtracting the background, and normalizing to the vehicle control. Three separate experiments obtained from different cultures (different animals) of primary neurons were performed. For each condition, six replicate wells were measured and the mean value was used for statistical analyses. Data was analyzed and plotted using Prism 5.0 (GraphPad Software Inc., La Jolla, Calif.).

Treatment of Cultured Primary Neurons with FAAH Inhibitors or Substrate—

The FAAH substrate, NAE 16:0 (N-palmitoylethanolamine), was emulsified in 40% 2-hydroxypropyl-β-cyclodextrin dissolved in DMSO by sonication at 50° C. to a final concentration of 50 mM. The FAAH inhibitors MAFP and URB597 were dissolved in DMSO at a concentration of 100 mM. Growth media was exchanged for 100 µl antioxidant-free media or antioxidant-free media containing vehicle or serial dilutions of substrate or inhibitor and plates were incubated as above. After an hour, 5 µl of $2 \times 10^{-8}$ cardanol-EA in anti-oxidant free media pre-diluted as above was added to the conditions indicated, plates were gently mixed and returned to the incubator. After another hour, oxidative stress was induced as described above. Viability assay, replicates, and analyses were performed as described above.

The use of the disclosed method is contemplated for use in conjunction with strategies to exacerbate cell death (e.g. combination therapy for existing oncology therapies such as enhancement of radiation and/or chemotherapy, surgery, and the like. The method may also be used in conjunction with chemo-sensitizing agents that are targeted at lipid-signaling pathways effected by disease processes or as a modulator of endocannabinoid signaling in applications ranging from cytoprotection to cellular development and excitable cell function. The method may be used for therapeutic applications where manipulation of localized endogenous NAE levels might be desired or in situ regulation of NAE metabolism. The method may be used for modulation of appetite and/or feeding behavior by decreasing the endogenous levels of acylethanolamide agonists in animal systems and/or clinical applications (e.g. weight loss therapy, agricultural applications to control drop damage by pests, etc.). The method may be used to decrease the level of NAEs in prokaryotic and/or eukaryotic cells, animals, humans, microorganisms by application of the compounds as pharmacological reagents that enhance NAE degradation.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for enhancing amidohydrolase activity of fatty acid amide hydrolase in a plant, the method comprising administering a phenoxyacyl-ethanolamide composition to a plant such that hydrolysis of N-acylethanolamines (NAEs) by fatty acid amide hydrolase (FAAH) in the plant is enhanced relative to a substantially identical plant that has not been administered with the phenoxyacyl-ethanolamide composition, wherein the phenoxyacyl-ethanolamide in the composition is represented by a structure:

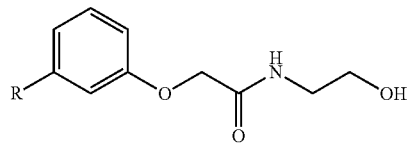

wherein R is an aliphatic side chain with between twelve and twenty carbons.

2. The method of claim 1, wherein the aliphatic side chain is un-branched and has fifteen carbons.

3. The method of claim 1, wherein the aliphatic side chain has at least one double bond.

4. The method of claim 1, wherein the aliphatic side chain has at least one double bond but no more than three double bonds.

5. The method of claim 1, wherein the aliphatic side chain is saturated.

6. The method of claim 1, wherein the aliphatic side chain has between thirteen and fifteen carbons.

7. The method of claim 1, wherein the aliphatic side chain has fifteen carbons.

8. The method of claim 1, wherein the aliphatic side chain is un-branched and has sixteen carbons.

9. The method as recited in claim 1, wherein the plant is a seedling.

10. The method as recited in claim 1, wherein the plant experiences exacerbated cell death relative to the substantially identical plant.

11. The method as recited in claim 1, wherein the plant experiences exacerbated cytostasis relative to the substantially identical the plant.

* * * * *